United States Patent [19]

Weisz et al.

[11] 4,093,029

[45] June 6, 1978

[54] UTILIZATION OF LOW BTU NATURAL GAS

[75] Inventors: Paul Burg Weisz, Yardley, Pa.; John Clarence Zahner, Princeton, N.J.

[73] Assignee: Mobil Oil Corporation, New York, N.Y.

[21] Appl. No.: 780,743

[22] Filed: Mar. 24, 1977

Related U.S. Application Data

[63] Continuation-in-part of Ser. No. 698,449, Jun. 21, 1976, abandoned.

[51] Int. Cl.$^2$ .............................................. E21B 43/16
[52] U.S. Cl. .............................. 166/305 R; 48/196 A; 48/214 A; 252/373; 260/449.5
[58] Field of Search ........... 48/196 A, 196 R, 214 A, 48/197 R, 206; 252/373; 260/449.5, 449.6; 166/274, 256, 266, 305 R

[56] References Cited

U.S. PATENT DOCUMENTS

| | | | |
|---|---|---|---|
| 3,442,332 | 5/1969 | Keith | 166/266 |
| 3,501,516 | 3/1970 | Parrish | 260/449.5 |
| 3,962,300 | 6/1976 | Hiller et al. | 260/449.5 |
| 3,964,545 | 6/1976 | Speller | 166/256 |

FOREIGN PATENT DOCUMENTS

| | | | |
|---|---|---|---|
| 1,262,987 | 3/1968 | Germany | 260/449.5 |
| 1,169,241 | 10/1969 | United Kingdom | 260/449.5 |

Primary Examiner—Robert L. Lindsay, Jr.
Assistant Examiner—George C. Yeung
Attorney, Agent, or Firm—Charles A. Huggett; Ronald J. Cier

[57] ABSTRACT

Natural gas having a high $CO_2$ content and low heating value is converted to useful and valuable products by the extensive removal of $CO_2$ followed by conversion of the residue to a liquid product useful as fuel (e.g. methanol) through a process combining steam reforming and conversion of the resultant reformer stream, which contains CO, $CO_2$ and $H_2$ to liquid products. The $CO_2$ removed from the natural gas feed is used, in a preferred embodiment, in tertiary methods of recovery of petroleum from natural reservoirs in which primary and secondary methods are no longer viable.

5 Claims, 1 Drawing Figure

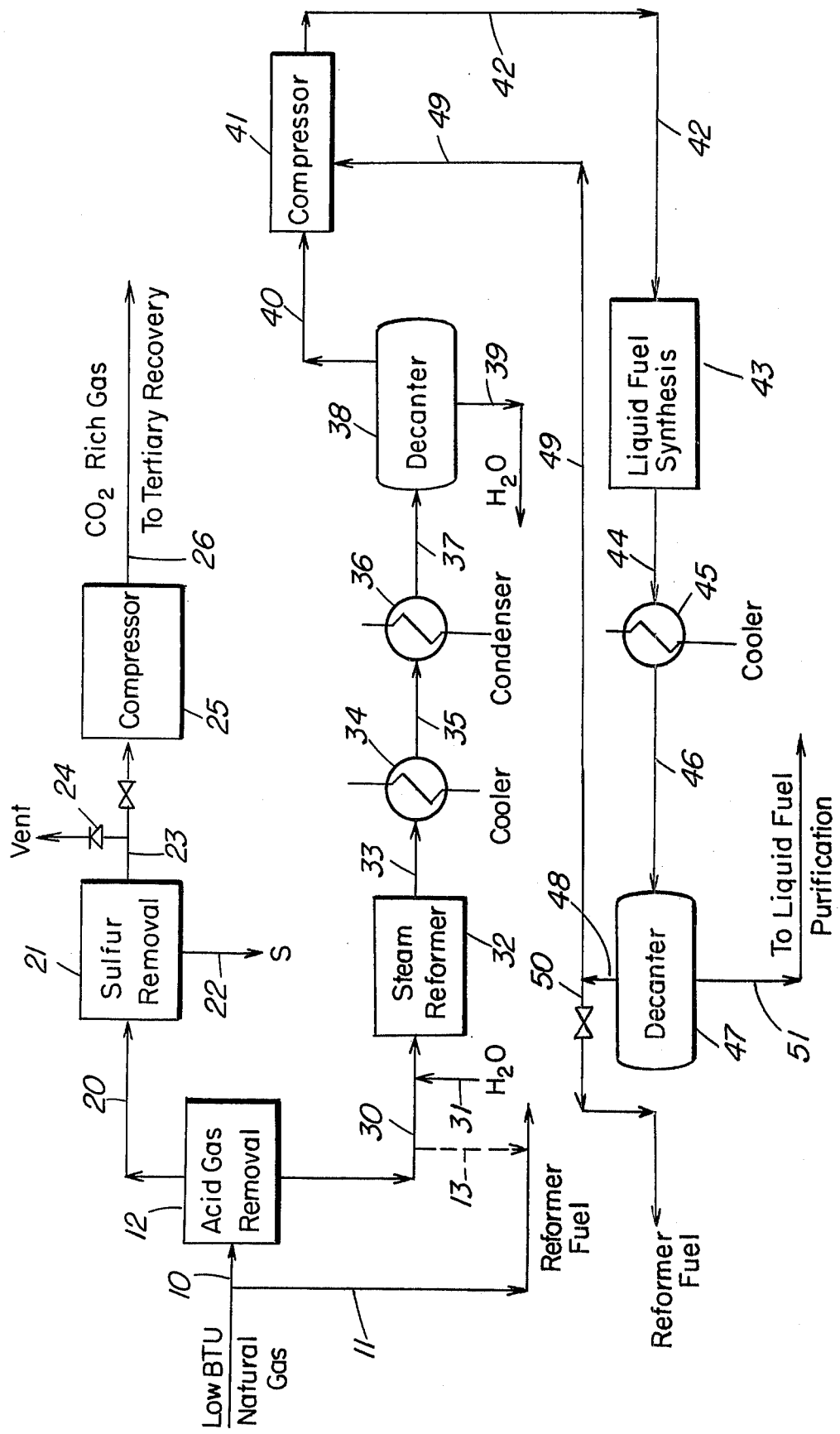

UTILIZATION OF LOW BTU NATURAL GAS

CROSS-REFERENCE TO RELATED APPLICATIONS

This application is a continuation-in-part of copending application Ser. No. 698,449 which was filed June 21, 1976, now abandoned.

BACKGROUND OF THE INVENTION

1. Field of the Invention

This invention relates to the utilization of natural gas, having a relatively high content of carbon dioxide in admixture with methane, to produce liquid fuel. In its preferred embodiment, the invention is also concerned with supply of a product gas stream rich in carbon dioxide and having reduced methane content as compared with the natural gas processed. Such product gas stream is utilized in tertiary methods of recovery of liquid petroleum from underground reservoirs which have been depleted to the extent viable by primary and secondary recovery methods.

2. Description of the Prior Art

The natural gases of interest in the process of this invention have previously been regarded as having no significant commercial value. Natural gas containing mixtures of carbon dioxide and methane in substantially equal volumes, and those containing a major proportion of methane, have been processed to separate the methane from the carbon dioxide and thus provide fuel gas of pipeline quality. However, it has been considered economically unrealistic to produce natural gas from extensive known reservoirs in which the gas contains a major proportion of carbon dioxide. The cost of the separation of the methane content of the gas from these reservoirs is too great, in comparison with the value of the recovered methane, to justify the construction and operation of separation facilities. Assuming a use for the carbon dioxide in tertiary recovery at petroleum reservoirs within a distance which can justify transporting the gas, such mixtures are unsuitable because of their content of methane which is known to inhibit solubility of carbon dioxide in petroleum.

In providing a combination of process steps which yield valuable products from natural gas previously considered valueless, the invention described herein utilizes known technology for:

(1) generating a synthesis gas of carbon monoxide and hydrogen primarily from the reaction of methane and water;

(2) synthesis of methanol or liquid hydrocarbons by reaction of carbon oxides and hydrogen; and (3) tertiary recovery of petroleum by injection of carbon dioxide, which contains little methane, into an underground reservoir, it being known that methane reduces the solubility of carbon dioxide in petroleum.

SUMMARY OF THE INVENTION

This invention provides a technique for the commercially practicable utilization of the previously valueless natural gases which contain upwards of fifty volume percent of carbon dioxide by a combination of steps which separate the natural gas feed into two separate streams and provide commercially useful products from both streams.

The first stream, the carbon dioxide content of which has been reduced to a level which is approximately optimal for subsequent methanol synthesis, is subjected to a reaction with water wherein the carbon content of the methane contained therein is converted into carbon monoxide in admixture with hydrogen. The resultant mixture is subjected to a synthesis reaction for the generation of liquid fuels such as methanol or hydrocarbons. The second stream, which comprises a substantial portion of the carbon dioxide from the natural gas feed, is sufficiently low in methane to be of significant utility in tertiary recovery of petroleum.

BRIEF DESCRIPTION OF THE DRAWING

The single FIGURE depicts a flow sheet of a typical process configuration in accord with the present invention.

DESCRIPTION OF THE PREFERRED EMBODIMENTS

As shown in the drawing, a stream of low BTU gas, produced from conventional wells, is supplied via line 10. Such a feed gas may contain, for example, 75% carbon dioxide and 25% methane by volume, usually admixed with small amounts of sulfur compounds, such compounds being primarily hydrogen sulfide. If this low BTU feed gas is sufficiently low in sulfur to meet environmental standards and to be within the sulfur tolerance limitation of the equipment, a portion may optionally be withdrawn by way of line 11 to serve as fuel for steam reformer 32.

The low BTU natural gas feed is passed via line 10 to acid gas removal means 12. Such acid gas removal means may be any conventional process for recovering hydrogen sulfide and carbon dioxide gases, such as the Rectisol process described by G. Ranke at pages 77–84 of Chemical Engineering World, Volume 9, Number 8, August, 1974. Essentially, the natural gas feed is brought into contact with a polar solvent (e.g. methanol) in a multiple-stage extraction process which removes substantially all of the sulfur-containing compounds ($H_2S$, COS, mercaptans, etc.) and most of the $CO_2$. The extraction parameters may be adjusted to control the amount of $CO_2$ and sulfur-containing compounds removed and thereby "tailor" the composition of the gas left behind to whatever $CO_2/CH_4$ mix is desired.

The acid gas removal means 12 is operated in such a manner as to produce a reformer feed gas for steam reformer 32 which comprises carbon dioxide and methane in approximately optimal proportions for subsequent liquid fuel synthesis step 43. For making methanol such optimal feed for the steam reformer is 20 to 40 mol percent carbon dioxide and 60 to 80 mol percent methane (i.e., 1.5 to 4 moles of $CH_4$ per mole of $CO_2$). A portion of this reformer feed gas may optionally be withdrawn by line 13 as fuel for steam reformer 32 should a fuel having a lower sulfur content then the low BTU natural gas feed be required.

The reformer feed gas is passed from the acid gas removal means 12, through line 30, to steam reformer 32 where the methane content is reacted with water to form hydrogen and carbon monoxide. The steam reformer is operated under conventional conditions to achieve the general overall reaction scheme:

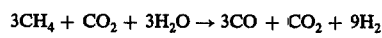

which is composed of sub-reactions:

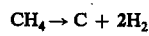 (a)

$$C + H_2O \rightarrow CO + H_2 \tag{b}$$

$$CH_4 + CO_2 \rightarrow 2CO + 2H_2 \tag{c}$$

Typical of steam reformer operations are temperatures of 650°–1010° C. (1200°–1850° F.) at pressures in the range of 14–42 kgs. per square centimeter (200–600 pounds per square inch) absolute. The reformer contains a catalyst suitable to promote such reaction (e.g. nickel oxide on alumina) and, in general, it is preferred to supply excess water to the reformer to protect the catalyst against coking. For the present purpose, it is suitable to provide a molar ratio of water to methane of about 1.2:1 to 2.4:1.

The product stream from reformer 32, which comprises CO, $CO_2$, $H_2$ and $H_2O$, passes via line 33 to cooler 34, where the mixture is reduced in temperature, and thence through line 35 to condenser 36. Water condensed in condenser 36 is removed in decanter 38 and recycled via line 39 for reuse in the process or is discharged from the system.

The gas phase from decanter 38 is transferred by line 40 to compressor 41, which may be of the multi-stage type with interstage cooling. Some water vapor in the effluent of decanter 38 may condense at interstage cooling and such condensate is preferably discharged for recycle or other disposition. The gas mixture (primarily CO, $CO_2$ and $H_2$) is compressed to a high pressure suitable to the synthesis reaction and passed by line 42 to liquid fuel synthesis reactor 43 for reaction of the carbon monoxide, carbon dioxide and hydrogen to produce methanol, hydrocarbons, or the like by known techniques. For example, methanol synthesis may be conducted at temperatures in the neighborhood of 200°–370° C (400°–700° F) and pressures of 28–105 kg/sq. cm. (400–1500 psia). Temperatures in the range of 218°–304° C (425°–580° F) are preferred.

The liquid fuel synthesis is carried out over a suitable catalyst, of which many are known in the art. Exemplary of such suitable catalysts would be partially reduced oxides of copper, zinc and chromium, zinc oxide and chromium oxide, zinc oxide and copper, copper and aluminum oxide or cerium oxide, zinc oxide and ferric hydroxide, zinc oxide and cupric oxide, a copper zinc alloy, and oxides of zinc, magnesium, cadmium, chromium, vanadium and/or tungsten with oxides of copper, silver, iron and/or cobalt, and the like. If the liquid fuel to be produced is methanol, the preferred catalyst is copper and zinc oxides on alumina. The reaction proceeds as follows:

$$CO + 2H_2 \rightarrow CH_3OH \tag{a}$$

$$CO_2 + 3H_2 \rightarrow CH_3OH + H_2O \tag{b}$$

$$CO_2 + H_2 \rightarrow CO + H_2O \tag{c}$$

The Fischer-Tropsch synthesis is well known to reduce carbon monoxide with hydrogen to hydrocarbons over potassium promoted iron catalyst. Newer techniques involve the use of a carbon monoxide reduction catalyst in combination with a porous crystalline aluminosilicate such as zerolite ZSM-5.

The carbon monoxide reduction is highly exothermic and requires extraction of heat to maintain suitable reaction temperatures. One technique for achieving this result is introduction of cold reactant at spaced points along the path of the reactor 43. For the purposes of this invention, it is preferred to dispose the catalyst in tubes within a vessel for generation of steam from water about the exterior of the tubes. This permits close control of temperatures and two stages of reaction, with the second stage at a lower temperature, by allowing steam to evolve at a lower pressure from the second stage vessel and thus promote completion of the reaction.

Effluent of reactor 43 at line 44, which is largely depleted of carbon monoxide, carbon dioxide and hydrogen content, passes to cooler 45 for condensation of the liquid fuel product. From cooler 45 the product stream passes via line 46 to decanter 47, from which the liquid fuel is withdrawn by line 51 for distillation and such other finishing steps as may be appropriate.

The gas phase from decanter 47 is separately withdrawn through lines 48 and 49 and recycled to compressor 41 for conversion of unreacted CO, $CO_2$ and $H_2$ to additional liquid product in reactor 43. From time to time it will be necessary to withdraw a portion of the gas phase from the system to maintain the concentration of inert substances (e.g. methane) at an acceptable level. This is accomplished by means of valved line 50. This purge stream may, upon discharge via valved line 50, be burned for its fuel value.

There are two product streams which result from acid gas removal means 12, the first being the aforedescribed reformer feed gas. The second product stream, which is taken off at line 20, comprises a substantial portion of the carbon dioxide and essentially all of the sulfur compounds from the low BTU natural gas feed. It is preferred that this $CO_2$-rich stream be further processed to provide a source of $CO_2$ valuable for use in tertiary methods of recovery of petroleum from subterranean oil-bearing formations and for other uses.

Should the sulfur compounds contained in the $CO_2$-rich stream be at an objectionable concentration, they may be removed by any of several variations of the conventional acid gas scrubbing technologies, such as selective extraction with liquid solvents, sorption on solid bodies and so forth, and such technology is not intended to be limiting in any way. Most conventional scrubbing systems can operate to give a $CO_2$-rich gas stream almost nil in $H_2S$ and a gas stream having a high concentration of the extracted sulfur compounds. When such sulfur removal is desired, the $CO_2$-rich stream contained in line 20 is passed to conventional sulfur removal stage 21 and the sulfur-rich stream obtained therefrom is withdrawn from the system by line 22 for subsequent recovery of the sulfur in a Claus Plant or other suitable means.

From here the $CO_2$-rich stream, the sulfur content of which is now reduced to an acceptable level, proceeds through line 23 and may take one of two directions. If further uses for the carbon dioxide are not economically attractive because of the location of the plant or other reason, the stream is discharged from the system through valved line 24. Preferably, the plant will be located within a reasonable distance of a subterranean petroleum-bearing formation and therefore the $CO_2$-rich stream becomes valuable for use in tertiary methods of recovery of the petroleum. In such case, the $CO_2$-rich stream is compressed at compressor 25 and continues through line 26 for use in tertiary recovery by techniques long known in the production art. See, for instance, U.S. Pat. No. 2,623,596, Whorton et al., Dec. 30, 1952.

A typical operation according to the invention is set forth in the Example below, based on computer calculations simulating the several reactions at equilibrium conditions. It will be recognized that any specific plant may vary somewhat from these results, depending largely on kinetic considerations.

EXAMPLE

The natural gas processed by computer simulation was that found in a field in Texas. The analysis of the gas is 75% carbon dioxide, 25% methane, with 50 ppm hydrogen sulfide. The gas is washed in a suitable absorption column (acid gas removal means 12) to remove 85% of the $CO_2$ content and all of the $H_2S$ content, to leave a reformer feed gas which is 31% $CO_2$ and 69% $CH_4$ by volume. This mixture of methane and carbon dioxide is reacted with water, over nickel oxide on alumina, at 850° C (1560° F) and 15.5 kg/sq. cm. (220 psi) absolute pressure. The compositions of the feed gas and product are shown in Table I.

TABLE I

Composition of Feed and Products in Steam Reforming

| | Reformer Feed Gas Moles | Reformer Product Moles |
|---|---|---|
| $H_2$ | | 249.93 |
| CO | | 81.11 |
| $CO_2$ | 45 | 46.65 |
| $H_2O$ | 240 | 155.59 |
| $CH_4$ | 100 | 17.24 |

The product from the steam reformer is cooled and the water content thereof removed. The remaining product is then converted to methanol at 260° C (500° F) and 52.7 kg/sq. cm. (750 psi), absolute pressure, over copper and zinc oxides on alumina at a recycle ratio of 4.8 volumes of gas effluent (stream 49) from decanter 47 per volume of fresh feed to the methanol synthesis reactor. Utilization of synthesis gas is 92.5% at a conversion per pass of 28.7%. Composition of the various streams is shown in Table II in moles. For convenience the reference numeral of the drawing at which each stream is found is noted in parenthesis on each column of the Table.

TABLE II

Composition of Streams in Moles

| | Fresh Feed (40) | Liquid Product (51) | Purge (50) | Recycle (49) | Combined Feed (42) | Reactor Exit (44) |
|---|---|---|---|---|---|---|
| CO | 81.11 | 0.12 | 4.75 | 153.67 | 234.78 | 159.00 |
| $CO_2$ | 46.65 | 3.71 | 15.20 | 491.60 | 538.25 | 511.71 |
| $H_2$ | 249.93 | 0.28 | 18.11 | 585.47 | 835.40 | 604.24 |
| $H_2O$ | 0.00 | 26.51 | 0.02 | 0.62 | 0.62 | 27.15 |
| $CH_3OH$ | 0.00 | 102.03 | 0.26 | 8.48 | 8.48 | 110.79 |
| $CH_4$ | 17.24 | 0.34 | 15.10 | 488.17 | 505.41 | 505.41 |

The $CO_2$ which is removed from the low BTU natural gas feed in the acid gas removal step is recovered from the wash liquid by subjecting the solution of $CO_2$ and sulfur compounds to reduced pressure and drawing off the overhead gas. The $CO_2$-rich stream obtained thereby, which comprises approximately 90–99% $CO_2$, 1–10% methane and 60 ppm $H_2S$, is then compressed and, having such drastically reduced methane content relative to the low BTU natural gas feed, is well-suited for tertiary recovery operations.

The foregoing is meant to be exemplary of the invention disclosed herein and is in no way limiting thereon. As one skilled in the art can readily appreciate, modifications and changes may be made in the embodiments herein described without departing from the scope and spirit of the invention.

What is claimed is:

1. A process for economic utilization of natural gas, having low heating value by reason of containing carbon dioxide in admixture with the methane content thereof, which process comprises subjecting a natural gas having substantial methane content in admixture with at least 50 volume percent of carbon dioxide based on total volume of said gas to the following steps in the sequence recited:

(a) removing a substantial portion of the acid gases from said natural gas to leave a reformer feed gas containing 20–40 mol percent carbon dioxide;

(b) mixing said reformer feed gas with water and reacting the mixture in contact with a catalyst to promote the reforming reaction of methane and water to produce carbon monoxide and hydrogen under temperature and pressure conditions conducive to said reforming reaction; and (c) reacting the product of step (b) in contact with a carbon monoxide reduction catalyst for promotion of synthesis reaction between carbon dioxide, carbon monoxide and hydrogen to produce methanol or hydrocarbons, which are liquid at normal temperature of 21° C (70° F) and atmospheric pressure, under conditions of temperature and pressure conducive of said synthesis.

2. The process of claim 1 wherein said reformer feed gas consists essentially of 1.5 to 4 moles of methane per mole of carbon dioxide.

3. The process of claim 1 wherein said acid gases removed from said natural gas feed are further processed to separate the sulfur-containing component therefrom and provide a gaseous by-product stream enriched in carbon dioxide as compared with said natural gas.

4. The process of claim 3 wherein said by-product stream is injected into a subterranean oil-bearing formation to enhance production of oil therefrom.

5. The process of claim 1 wherein said acid gases removed from said natural gas feed, comprising a gaseous by-product stream enriched in carbon dioxide as compared with said natural gas, are injected into a subterranean oil-bearing formation to enhance production of oil therefrom.

* * * * *